US011793457B2

(12) United States Patent
Cipriano et al.

(10) Patent No.: US 11,793,457 B2
(45) Date of Patent: Oct. 24, 2023

(54) INFANT WARMING SYSTEM HAVING ECG MONITOR AND METHOD FOR PROVIDING RESUSCITATION ASSISTANCE

(71) Applicant: General Electric Company, Schenectady, NY (US)

(72) Inventors: James Patrick Cipriano, Laurel, MD (US); Thomas Charles Underwood, Sykesville, MD (US); Steven Mitchell Falk, Baltimore, MD (US); Muge Pirtini Cetingul, Menomonee Falls, WI (US); Karen P. Starr, Phoenix, MD (US)

(73) Assignee: General Electric Company, Schenectady, NY (US)

( * ) Notice: Subject to any disclaimer, the term of this patent is extended or adjusted under 35 U.S.C. 154(b) by 113 days.

(21) Appl. No.: 17/492,066

(22) Filed: Oct. 1, 2021

(65) Prior Publication Data

US 2022/0015697 A1 Jan. 20, 2022

Related U.S. Application Data

(63) Continuation of application No. 15/630,714, filed on Jun. 22, 2017, now Pat. No. 11,141,104.

(51) Int. Cl.
*A61B 5/00* (2006.01)
*A61F 7/00* (2006.01)
(Continued)

(52) U.S. Cl.
CPC .......... *A61B 5/4836* (2013.01); *A61B 5/0245* (2013.01); *A61B 5/14551* (2013.01); *A61B 5/25* (2021.01); *A61B 5/30* (2021.01); *A61B 5/316* (2021.01); *A61B 5/339* (2021.01); *A61B 5/741* (2013.01); *A61B 5/746* (2013.01); *A61B 5/7435* (2013.01); *A61F 7/00* (2013.01); *A61F 7/007* (2013.01); *A61G 11/00* (2013.01);
(Continued)

(58) Field of Classification Search
None
See application file for complete search history.

(56) References Cited

U.S. PATENT DOCUMENTS 3,888,240 A * 6/1975 Reinhold, Jr. ....... A61B 5/6831
600/536
4,588,383 A * 5/1986 Parker ................. G09B 23/288
601/41
(Continued)

*Primary Examiner* — Shirley X Jian

(57) ABSTRACT

An infant warming system comprising a platform for supporting an infant, at least two chest electrodes configured to connect to and detect cardiac potentials from a chest of the infant, an ECG monitor configured to receive the cardiac potentials from the at least two chest electrodes and determine a heart rate based on the cardiac potentials, a pulse oximeter device configured to determine an $SpO_2$ for the infant, and a processor configured to compare the heart rate for the infant to a first heart rate threshold and compare the $SpO_2$ for the infant to a first $SpO_2$ threshold. The processor can also adjust a display of the heart rate and the $SpO_2$ on a display device based on the comparisons and generate a first care instruction via a user interface based on the heart rate, the $SpO_2$, or a combination thereof.

18 Claims, 10 Drawing Sheets

(51) Int. Cl.
*A61G 11/00* (2006.01)
*A61M 16/00* (2006.01)
*A61M 16/04* (2006.01)
*A61B 5/0245* (2006.01)
*A61B 5/1455* (2006.01)
*A61N 5/06* (2006.01)
*G16H 50/30* (2018.01)
*G16H 40/63* (2018.01)
*A61H 31/00* (2006.01)
*G16H 20/40* (2018.01)
*A61B 5/25* (2021.01)
*A61B 5/30* (2021.01)
*A61B 5/316* (2021.01)
*A61B 5/339* (2021.01)
*A61B 5/0205* (2006.01)
*A61B 5/01* (2006.01)

(52) U.S. Cl.
CPC .......... *A61G 11/005* (2013.01); *A61H 31/00* (2013.01); *A61M 16/00* (2013.01); *A61M 16/0051* (2013.01); *A61M 16/0057* (2013.01); *A61M 16/022* (2017.08); *A61M 16/04* (2013.01); *A61N 5/0625* (2013.01); *G16H 20/40* (2018.01); *G16H 40/63* (2018.01); *G16H 50/30* (2018.01); *A61B 5/01* (2013.01); *A61B 5/0205* (2013.01); *A61B 5/749* (2013.01); *A61B 5/7475* (2013.01); *A61B 2503/045* (2013.01); *A61B 2560/0462* (2013.01); *A61F 2007/0088* (2013.01); *A61G 2203/20* (2013.01); *A61G 2203/30* (2013.01); *A61G 2203/46* (2013.01); *A61H 2230/045* (2013.01); *A61M 2202/0208* (2013.01); *A61M 2205/052* (2013.01); *A61M 2205/505* (2013.01); *A61M 2205/581* (2013.01); *A61M 2205/583* (2013.01); *A61M 2230/04* (2013.01); *A61M 2230/06* (2013.01); *A61M 2230/205* (2013.01); *A61M 2230/50* (2013.01); *A61M 2240/00* (2013.01); *A61N 2005/0637* (2013.01); *A61N 2005/0659* (2013.01)

(56) References Cited

U.S. PATENT DOCUMENTS

| | | | | |
|---|---|---|---|---|
| 5,913,685 A * | 6/1999 | Hutchins | ............... | G09B 23/288 434/265 |
| 6,409,654 B1 * | 6/2002 | McClain | ............... | G16H 80/00 5/655 |
| 6,453,186 B1 * | 9/2002 | Lovejoy | ............... | A61B 5/282 600/386 |
| 6,697,671 B1 * | 2/2004 | Nova | ............... | A61N 1/39044 607/5 |
| 8,002,701 B2 * | 8/2011 | John | ............... | G16H 40/67 128/903 |
| 8,369,924 B1 * | 2/2013 | Chang | ............... | A61B 5/282 600/509 |
| 8,660,630 B2 * | 2/2014 | Chang | ............... | A61B 5/0006 600/509 |
| 8,689,788 B2 * | 4/2014 | Rabi | ............... | A61P 11/00 128/204.23 |
| 8,727,980 B2 * | 5/2014 | Coelho | ............... | A61B 5/0205 600/301 |
| 9,220,443 B2 * | 12/2015 | Silver | ............... | A61H 31/00 |
| 9,289,166 B2 * | 3/2016 | Ito | ............... | A61B 5/1455 |
| 9,521,977 B2 * | 12/2016 | Silver | ............... | A61B 5/486 |
| 9,554,958 B2 * | 1/2017 | Richards | ............... | A61G 11/00 |
| 9,649,333 B2 * | 5/2017 | Rabi | ............... | A61M 16/12 |
| 9,713,445 B2 * | 7/2017 | Freeman | ............... | A61B 5/4836 |
| 9,872,807 B2 * | 1/2018 | Falk | ............... | G16H 40/63 |
| 9,931,042 B2 * | 4/2018 | Mahar | ............... | A61B 5/1135 |
| 10,110,859 B2 * | 10/2018 | Kaestle | ............... | G06V 40/19 |
| 10,143,621 B2 * | 12/2018 | Silver | ............... | A61H 31/007 |
| 10,322,060 B2 * | 6/2019 | Fleischacker | ............... | A61N 1/3993 |
| 10,413,476 B2 * | 9/2019 | Giarracco | ............... | A61B 5/7235 |
| 11,141,104 B2 * | 10/2021 | Pirtini Cetingul | ............... | A61B 5/0245 |
| 2002/0124295 A1 * | 9/2002 | Fenwick | ............... | A41D 13/1245 2/69 |
| 2003/0095263 A1 * | 5/2003 | Varshneya | ............... | A61B 5/4818 356/477 |
| 2005/0215845 A1 * | 9/2005 | Mahony | ............... | A61B 5/002 600/22 |
| 2007/0213600 A1 * | 9/2007 | John | ............... | A61B 5/02028 600/300 |
| 2007/0276273 A1 * | 11/2007 | Watson, Jr. | ............... | A61B 5/282 600/391 |
| 2008/0125821 A1 * | 5/2008 | Blomquist | ............... | A61N 1/39044 601/41 |
| 2008/0281168 A1 * | 11/2008 | Gibson | ............... | A61B 5/002 600/301 |
| 2010/0080431 A1 * | 4/2010 | Datema | ............... | A61B 5/6887 5/601 |
| 2011/0190611 A1 * | 8/2011 | Rabi | ............... | A61M 16/125 128/207.14 |
| 2011/0270100 A1 * | 11/2011 | Chang | ............... | A61B 5/0006 600/509 |
| 2012/0035675 A1 * | 2/2012 | Walker | ............... | A61N 1/39044 607/3 |
| 2012/0232357 A1 * | 9/2012 | Coelho | ............... | A61B 5/72 600/301 |
| 2012/0265040 A1 * | 10/2012 | Ito | ............... | G16H 50/20 600/323 |
| 2012/0302910 A1 * | 11/2012 | Freeman | ............... | G16H 20/40 128/205.13 |
| 2013/0150655 A1 * | 6/2013 | Ten Eyck | ............... | A61G 11/009 600/22 |
| 2014/0000609 A1 * | 1/2014 | Steinhauer | ............... | A61M 16/0057 128/204.23 |
| 2015/0105636 A1 * | 4/2015 | Hayman | ............... | A61B 5/742 600/323 |
| 2016/0112681 A1 * | 4/2016 | Kaestle | ............... | G16H 30/40 348/78 |
| 2016/0117901 A1 * | 4/2016 | Zhang | ............... | G16H 50/20 340/286.07 |
| 2016/0135758 A1 * | 5/2016 | Sabota | ............... | A61B 5/7405 340/573.1 |
| 2016/0206504 A1 * | 7/2016 | Giarracco | ............... | A61B 5/14551 |
| 2016/0287470 A1 * | 10/2016 | Lewis | ............... | A61B 5/6805 |
| 2016/0302719 A1 * | 10/2016 | Ezeuka | ............... | A61B 5/14552 |
| 2017/0065484 A1 * | 3/2017 | Addison | ............... | A61B 5/7264 |
| 2017/0068791 A1 * | 3/2017 | Hermann | ............... | A61N 1/3987 |
| 2017/0112422 A1 * | 4/2017 | Hatch | ............... | A61B 5/14552 |
| 2017/0156608 A1 * | 6/2017 | Mahar | ............... | A61B 5/1135 |
| 2017/0252571 A1 * | 9/2017 | Dascoli | ............... | A61N 1/3925 |
| 2017/0266399 A1 * | 9/2017 | Campana | ............... | A61M 16/107 |
| 2017/0347960 A1 * | 12/2017 | Falk | ............... | A61B 5/1102 |
| 2018/0040255 A1 * | 2/2018 | Freeman | ............... | A61B 5/021 |
| 2018/0078163 A1 * | 3/2018 | Welch | ............... | A61B 5/0002 |
| 2018/0360324 A1 * | 12/2018 | Lorraine | ............... | A61B 5/0245 |
| 2018/0368762 A1 * | 12/2018 | Pirtini Cetingul | ............... | A61B 5/7435 |
| 2019/0269574 A1 * | 9/2019 | Lurie | ............... | A61H 31/005 |

* cited by examiner

INFANT WARMING SYSTEM HAVING ECG MONITOR AND METHOD FOR PROVIDING RESUSCITATION ASSISTANCE

CROSS-REFERENCE TO RELATED APPLICATIONS

The present application is a continuation of and claims priority to U.S. patent application Ser. No. 15/630,714, filed on Jun. 22, 2017, which is incorporated herein by reference in its entirety.

BACKGROUND

The present disclosure relates to infant warming systems, such as radiant warmers and hybrid devices including an incubator and radiant warmer. And more specifically to systems and methods for controlling such warming systems for providing medical care to newborn infants immediately upon birth.

At the time of birth, infants need immediate assessment and care, including assessment of heart and respiratory function. Infant patients can experience relatively rapid changes in condition, especially immediately after birth. Depending on the infant's condition, various therapies may be provided, including resuscitation or other respiratory care.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an infant warming system includes a frame structure, a platform for supporting an infant that is connected to the frame structure, a radiant warmer supported on the frame structure above the platform, an ECG connection port configured to connect to ECG electrodes, and an ECG monitor housed on the frame structure, the ECG monitor receiving cardiac potentials from the ECG electrodes connected to the infant. The infant warming system further includes a control system configured to process the cardiac potentials to detect each heart beat of the infant, calculate a heart rate for the infant based on a detected heart beats, and display the heart rate on a display device associated with the infant warming system.

Another exemplary embodiment of an infant warming system includes a platform for supporting an infant, a heating system for warming the infant on the platform, and an ECG monitor receiving cardiac potentials from at least two electrodes connected to the infant and determining the heart rate based on the cardiac potentials. The infant warming system further includes a display device that displays the heart rate and a resuscitation module configured to compare the heart rate for the infant to at least one heart rate threshold, adjust the display of the heart rate on the display device based on the comparison, and to generate a care instruction via a user interface based on the heart rate.

One embodiment of the method of operating and infant warming system is provided, wherein the infant warming system comprises an ECG monitor to detect a heart rate and user interface comprising at least one of a display device and a speaker. The method includes detecting one of two or more ECG electrodes on the infant to an ECG connection port in communication with the ECG monitor, and determining a heart rate for the infant based on cardiac potentials sensed via the ECG electrodes. The method further includes determining that the heart rate is below a first heart rate threshold, and then generating a first care instruction and first care option via the user interface based on the heart rate. The method further includes detecting that the heart rate remains below the first heart rate threshold for at least a predetermined time or that the heart rate is below a second heart rate threshold, and then generating a second care instruction and a second care option via the user interface.

Various other features, objects, and advantages of the invention will be made apparent from the following description taken together with the drawings.

DETAILED DESCRIPTION

Figure 1:
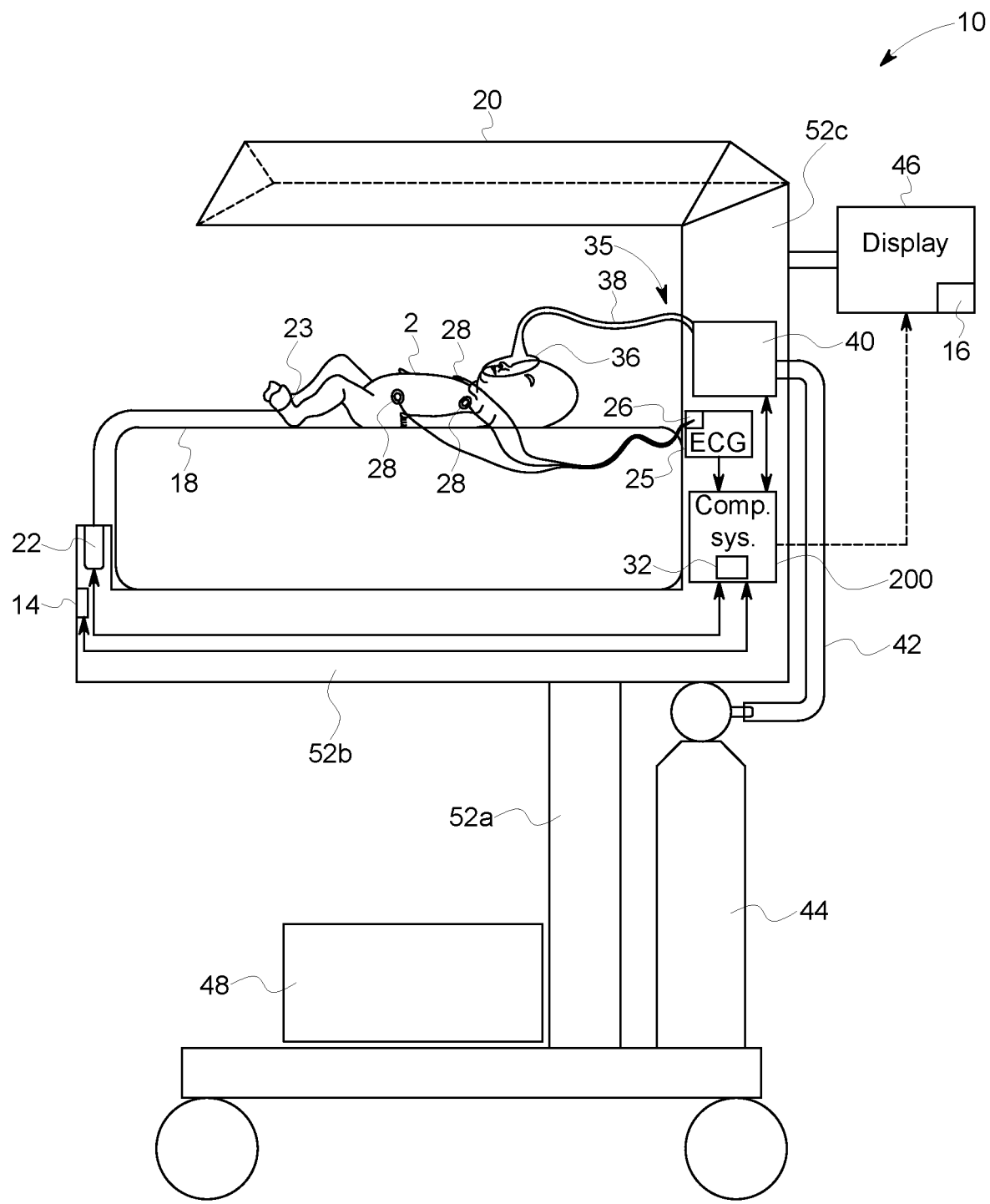
FIGS. 1 and 2 provide exemplary infant warming systems according to the present disclosure.

In light of their experimentation and research in the relevant field, the present inventors have recognized that clinicians providing care to infants at birth are often seeking more guidance for providing safe, resuscitative care to infants, such as to instructions on when to further or discontinue treatment actions. Current systems for providing newborn resuscitation do not enable sufficient cardiac and non-invasive respiratory monitoring necessary to provide consistent and optimal resuscitative care to a newborn, including failing to provide reliable heart rate information, such as ECG-based heart rate information. In light of these problems and needs in the relevant field recognized by the inventors, they developed the disclosed warming system providing ECG-based resuscitation support. The inventors have recognized that integration of ECG technology into a warming device can be utilized to provide a comprehensive care system for a newborn infant, especially for providing respiratory and resuscitative care for infants that need immediate medical attention at the first few minutes of birth.

When an infant is born in need of immediate medical care, a high pressure environment ensues with a lot of elements to be considered and managed, typically involving a number of different caretakers participating in caring for the infant. Accordingly, the inventors recognized that clinicians may benefit from assistance in managing information and decision making regarding the resuscitation workflow—e.g., minimizing distractions and highlighting necessary information—facilitating the caregiver in making clinical decisions quickly and accurately.

Upon recognition of the forgoing challenges and the needs in the relevant field, the inventors have developed the disclosed infant warming system having an integrated ECG monitor and associated method for controlling the warming system to provide resuscitation guidance, such as based on heart rate. An ECG monitor is housed within the frame structure of the infant warming system and receives cardiac potentials from at least two electrodes connected to the infant, who is laying on the platform of the infant warming system. The infant warming system calculates the heart rate for the infant based on detected heart beats within the cardiac potentials, and controls a display associated with the infant warming device to display the heart rate. The display may be adjusted based on the heart rate in order to prioritize the heart rate on the display when the heart rate falls to a dangerous level, such as by increasing the size of the heart rate on the display and/or placing the heart rate in a more prominent position on the display.

Additionally, the warming device may operate in a resuscitation mode to determine and generate a care instruction based on the heart rate and/or a stage of caring for the infant within the first few minutes of birth. To provide just a few examples, the care instruction may advise a clinician to monitor respiration, to supplement or increase oxygen ($O_2$) being provided to the infant, to provide positive pressure ventilation (PPV) to the infant, to intubate or administer a laryngeal mask to the infant, to begin or end chest compressions in the infant, or the like.

These systems can further be configured to provide audible instructions to the user and/or audible enunciation of the heart rate and other physiological information, and to suppress audible enunciation of alarms and other auditory distractions. The system may further be configured with a microphone to record audible inputs from a clinician, such as an acknowledgement of execution of a care instruction and/or a care option selection audibly announced by a clinician while performing care on the infant.

Figure 2:
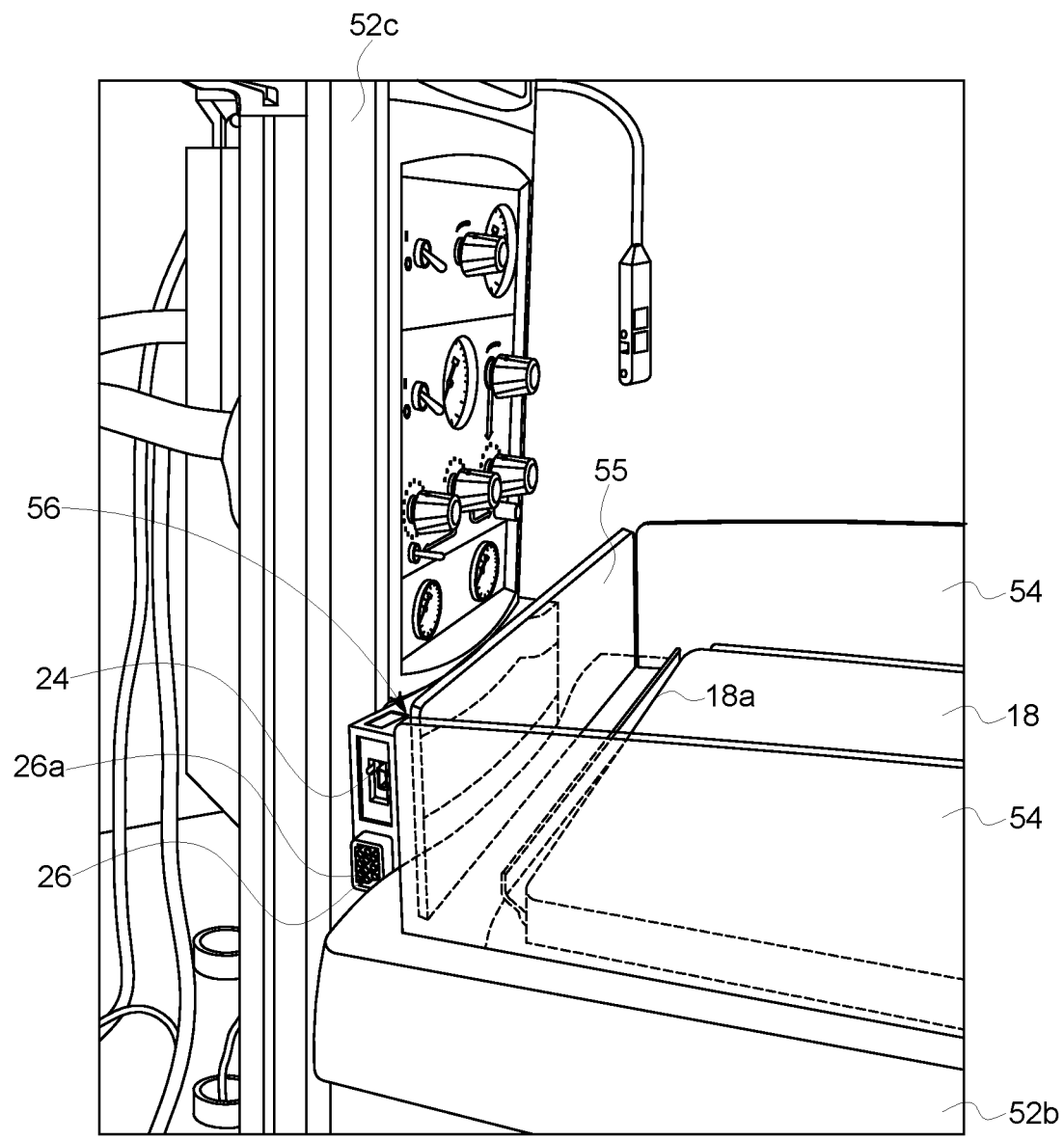

Various embodiments, features, and advantages of the disclosed system and method are discussed herein with respect to FIGS. 1 through 9. FIGS. 1 and 2 depict exemplary infant warming systems 10. In the embodiment of FIG. 1, the exemplary infant warming system 10 is a radiant warmer having a warmer system 20 that includes a radiant heater that directs infrared energy towards the infant 2 in order to provide a heated environment for the infant 1. In other embodiments, the infant warming system 10 may include an incubator system, alone or in combination with a radiant warmer, where a canopy is provided over the platform 18 supporting the infant 2 to form a micro environmental chamber providing a controlled and isolated environment. However, the infant warming system 10 preferably provides easy and unimpeded access to the infant 2 for purposes of providing resuscitative and ventilation care within the first few minutes of birth. The position of the infant in FIG. 1 is not intended to be indicative or representative of actual or appropriate positioning of an infant for resuscitation. When performing resuscitative and ventilation care to an infant in the first few minutes of birth, the infant 2 is often placed with their head proximal to the bottom, or foot side, of the platform 18.

The exemplary warming system 10 comprises a frame structure 52, which provides structural support for and houses the various aspects of the warming system 10. The frame structure 52, for example, may include structural support elements supporting the weight of the system components, as well as exterior or casing elements that enclose and protect the system components and/or provide an attractive facade. In the example shown at FIG. 1, the frame structure 52 includes a base portion 52a (which may support and/or house various aspects of the system, such as a battery 48 and/or a gas supply tank 44), a platform support structure 52b portion that supports the platform 18 on which the infant 2 lays, and a vertical panel structure 52c (which may support various user interface and control systems, for example, as well as systems for providing therapy and care to the infant, such as a ventilator device 40, an ECG monitor 25, a warming system 20, a $SpO_2$ monitor 22, etc.). The schematic diagram of FIG. 1 is for purposes of exemplifying just one embodiment of the warming system 10 the present disclosure, and in other embodiments the system 10 may include any of various additional system elements and the system elements may be arranged on the frame structure 52 in various ways not exemplified in the schematic diagram provided in FIG. 1.

Devices and systems for monitoring and providing resuscitation and other therapies to the infant 2 are incorporated into the infant warming system 10. In the depicted embodiment, the infant warming system 10 includes and ECG monitor 25 housed on the frame structure 52. The ECG monitor 25 receives cardiac potentials via ECG electrodes connected to the infant. In the depicted embodiment, the ECG monitor 25 receives cardiac potentials from three electrodes 28 connected to the infant 2 at the right arm RA, left arm LA, and left leg LL positions. In other embodiments, the ECG monitor may receive cardiac potentials from any number of two or more electrodes connected to the infant in any of various electrode arrangements. The ECG electrodes 28 are connected to the ECG monitor 25 via an ECG connection port 26 configured to receive connectors of the two or more ECG electrodes 28. As depicted in FIG. 2, the ECG connection port 26 may be positioned on and provided at a portion of the frame structure 52 that is proximal to a head of the platform 18. In various embodiments, the ECG connection port 26 may take any of various forms. The ECG electrode connection port provides a physical contact point 26a for connection with each electrode 28, which may be bundled together in a single connector that mates with ECG connection port 26, or each electrode 28 may have a separate connector that mates with and is separately received by the ECG connection port 26. In still other embodiments, the ECG electrodes 28 may be wireless electrodes, and in such an embodiment the ECG connection port 26 may comprise one or more wireless receiver transmitters in communication with two or more ECG wireless electrodes.

The ECG connection port 26 may be provided at any location on the infant warming system 10. In one embodiment, the ECG connection port 26 is provided on a portion of the frame structure 52 that is proximal to a head 18a of the platform 18, such as on the vertical panel structure 52C. In the embodiment of FIG. 2, the platform 18 is surrounded by at least three walls (which, for example, may be comprised of translucent or transparent material), including two side walls 54 and a head wall 55. In the depicted embodiment a gap 56 is provided between the head wall 55 and each of the side walls 54, which can allow for passage of the wires of the ECG electrodes connecting between the infant 2 and the ECG connection port 26. In other embodiments, the ECG connection port 26 may be provided at any other location on the frame structure. To provide just one additional example, the ECG connection port 26 may be provided on the platform support structure 52b such as proximal to a foot side of the platform 18.

The infant warming system 10 may further include a pulse oximeter device 22, including a $SpO_2$ sensor 23 attachable to the infant 2 to measure, or provide an estimate of, oxygen saturation ($SpO_2$) value. The pulse oximeter device 22 may be incorporated into and provided at any location on the frame structure 52. In the schematic depiction of an exemplary embodiment in FIG. 1, the pulse oximeter 22 is provided on the platform support structure 52b, and specifically at a location proximal to a foot side of the platform 18.

However, in other embodiments the pulse oximeter and/or a connection for the sensor 23 may be provided at any location on the frame structure 52, such as on the vertical panel structure 52C. FIG. 2 provides such example, where a $SpO_2$ sensor port 24 is provided on the vertical panel structure 52c adjacent to the ECG connection port 26. In still other embodiments, the $SpO_2$ sensor 23 may be a wireless device configured to wirelessly transmit $SpO_2$ measurement values to a receiver transmitter incorporated within the system 10.

In FIG. 1, the ECG monitor 25 and the pulse oximeter device 22 are depicted as separate devices that calculate respective monitoring values for the infant 2 and transmit such values to the computing system 200. Such communication may be provided by any wired or wireless means. In still other embodiments, some or all of the physical circuitry and/or software comprising the pulse oximeter 22 and/or the ECG monitor 25 may be incorporated within the computing system 200. In general, the control system for the warming system 10 may comprise several separate computing systems, or control sub-systems, in the ECG monitor 25, the pulse oximeter device 22, the ventilator device 40, the computing system 200, and/or various other control sub-systems for controlling various aspects of the system 10, such as a display control sub-system, a speaker control sub-system, an auditory processing system associated with the microphone 14, etc. In various embodiments, all such sub-systems may be provided on separate hardware systems, or any or all of them may be combined together on in single set of hardware and software, and together may be generally referred to herein as the control system for the warming system 10.

The warming system 10 may further include devices and systems for providing ventilation support for the infant. In the schematic example of FIG. 1, a breathing circuit 35 for providing gas to the infant 2 includes a ventilator device 40, such as a continuous positive airway pressure (CPAP) device, a positive pressure ventilation (PPV) device, or a positive end expiratory pressure (PEEP) device (or a ventilator device providing all three respiratory therapies). In the embodiment, the ventilator device 40 receives a gas supply from supply line 42 connected to gas supply tank 44 supported on the base structure 52a. The ventilator device 40 regulates the gas supply as appropriate to provide resuscitative and/or respiratory assistance to the infant 2. In the depicted scenario, the ventilator device 40 connects to a breathing tube 38 supplying gas to the infant through a mask 36 applied over the infant's nose and mouth. In other embodiments, gas may be delivered to the patient via another device, such as an endotracheal tube, a laryngeal mask, nasal cannula, or the like, and any such gas delivery element or system may connect to the breathing tube 38 in order to deliver gas from the gas supply 44 to the patient.

The infant warming system 10 may include a battery 48 to power the various systems and devices thereon. The battery 48 may be positioned, for example, on the base structure 52a, such as at a location that is easily accessible in order to recharge or replace that battery 48. The charging status of the battery may be monitored by a power control module, such as may be provided separately from and in communication with, or otherwise incorporated into, the computing system 200. The computing system 200 may provide a battery status notification, such as on the display device 46. Alternatively, or additionally, the infant warming system 20 may receive power from a grid system such as being plugged into an outlet connected to the AC power grid for the health care facility.

The warming system 10 may include various user interface devices for controlling various aspects of the system. Such user interface devices may include a display device 46 controllable to provide physiological information about the infant 2 and/or the status of various aspects of the system. For example, the display 46 may be controllable by the computing system 200 to display a heart rate, and $SpO_2$, a pulse rate, a temperature, or any other physiological information measured from the patient. Additionally, the display device 46 may be controlled to display information regarding the heater system 20, ventilator device 40, ECG monitor 25, or pulse oximeter device 22, such as the mode of operation or other pertinent regarding those systems and devices. In certain embodiments, the display device 46 may be a touch screen capable of providing user control inputs through which a clinician can control the various systems and devices comprising the infant warming system 10. Exemplary user interfaces are provided at FIGS. 4A-4C herein.

The infant warming system 10 may further include a microphone 14 configured to detect voice inputs from a clinician, such as during operation of the system in resuscitation mode as described herein. The system may further include a speaker 16, which may be incorporated into the display device 46 or elsewhere on the infant warming system, that produces audible alerts, alarms, instructions, or the like to facilitate care of the infant.

The infant warming system 10 is beneficially configured to receive cardiac potentials and reliably calculate a heart rate for the infant based on the cardiac potentials. The infant warming system 10 incorporates one or more sets of software instructions executable on one or more processors to carry out various calculations and control steps, various embodiments and examples of which are described herein. The heart rate module 30 is configured to process the cardiac potentials received from the ECG electrodes 28 to detect a heart beat of the infant 2. The heart rate 80 can then be calculated by the heart rate module 30 based on the intervals between the detected heart beats. For example, the heart rate 80 for the infant may be calculated by filtering and/or averaging the detected heart beat intervals over a period of time. The heart rate 80 value may then be packetized and transported between various aspects of the control system, such as sub-modules executing various aspects of the overall control system and/or the user interface. The system may further include a resuscitation module 32 comprising executable software instructions for system control that provide a tailored environment and system optimized for resuscitative or ventilation support within the first few minutes after the infant's birth. Various possible control features and aspects provided by the resuscitation module 32 are discussed herein.

Figure 3:
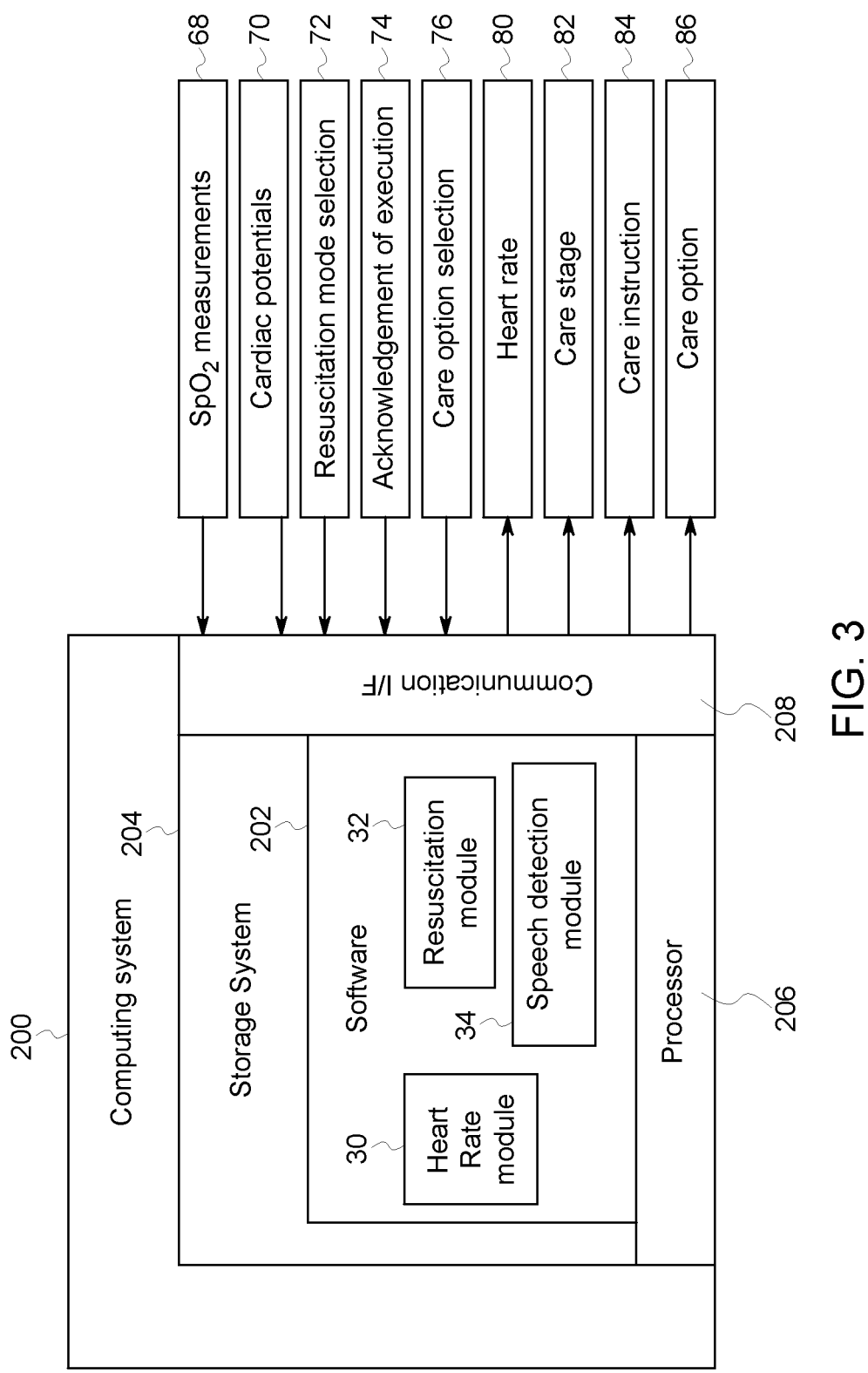
FIG. 3 depicts an exemplary computing system associated with an infant warming system.

FIG. 3 provides a schematic diagram of an exemplary computing system 200 associated with or comprised in the infant warming system 10 that operates as described herein. In the depicted embodiment, the computing system 200 incorporates a heart rate module 30 that calculates a heart rate 80 for the infant 2 based on cardiac potential 70 received via ECG electrodes 28. The computing system 200 further incorporates a resuscitation module 32 comprising several instructions executable to determine a care stage for the infant 2 based on the heart rate 80 and/or to generate one or more care instructions 84 via the display 46 and/or the speaker 16 to assist a clinician in providing resuscitative care to the infant 2. Exemplary care instructions 84 could include a monitor respiration instruction (e.g., an auditory or visual announcement is provided via the user interface instructing a clinician to observe the respiration qualities), a positive pressure ventilation instruction (e.g., instructing application of a mask or other interface between the breathing circuit, a ventilation pressure or rate, or the like), a supplement $O_2$ instruction (e.g., a percentage of oxygen to the supplied to the infant via the breathing circuit), an intubation instruction (e.g., an instruction to intubate the infant), and a chest compression instruction (e.g. an instruction to start or stop chest compressions, a compression rate or pressure, or the like).

The resuscitation module 32 may be activated upon receipt of a resuscitation mode selection 72 by a clinician via a user interface on the warming system 10, such as via touching a selection area provided on a touch screen display device 46 or via a voice instruction sensed by the microphone 14. For example, the resuscitation module 32 in conjunction with the speech detection module 34 may be configured to detect an auditory resuscitation mode selection 72 voiced by a clinician providing care to the infant 2. In various embodiments, the speech detection module 34 may be comprised of any speech or voice recognition software, such as computer executable instructions configured to detect any of certain words, phrases, or other audible commands that are likely to be provided by a clinician in order to activate the resuscitation module 32, provide an acknowledgement of execution 74 of certain actions or care steps, and/or a care option selection 76 selecting from care options 86 provided by the resuscitation module 32. Such user inputs are described in more detail herein below. The resuscitation module 32 may further be configured to receive $SpO_2$ measurements 68 and/or other physiological inputs from the patient.

For example, the resuscitation module 32 may be configured to compare the heart rate to at least one heart rate threshold for the infant and to determine a care stage—e.g., select one of a predetermined set of care stages—based on the current heart rate and/or based on the history or trend of heart rate measurements. The care stage may dictate certain care instructions 84 and/or care options 86 which may be provided to a clinician caring for the infant 2. The activation thresholds set a threshold value for the heart rate and the $SpO_2$ upon which the resuscitation module is automatically activated in order to provide care guidance to a clinician based at least on the heart rate. The resuscitation module may also be manually activatable by a clinician, such as through the user interface of the warming system. For example, the warming system may be configured to receive a resuscitation mode selection 72 from a clinician, either through a selection on a touch screen display device 46 and/or via detection of an audible command from the clinician via the microphone 14.

Figure 5:
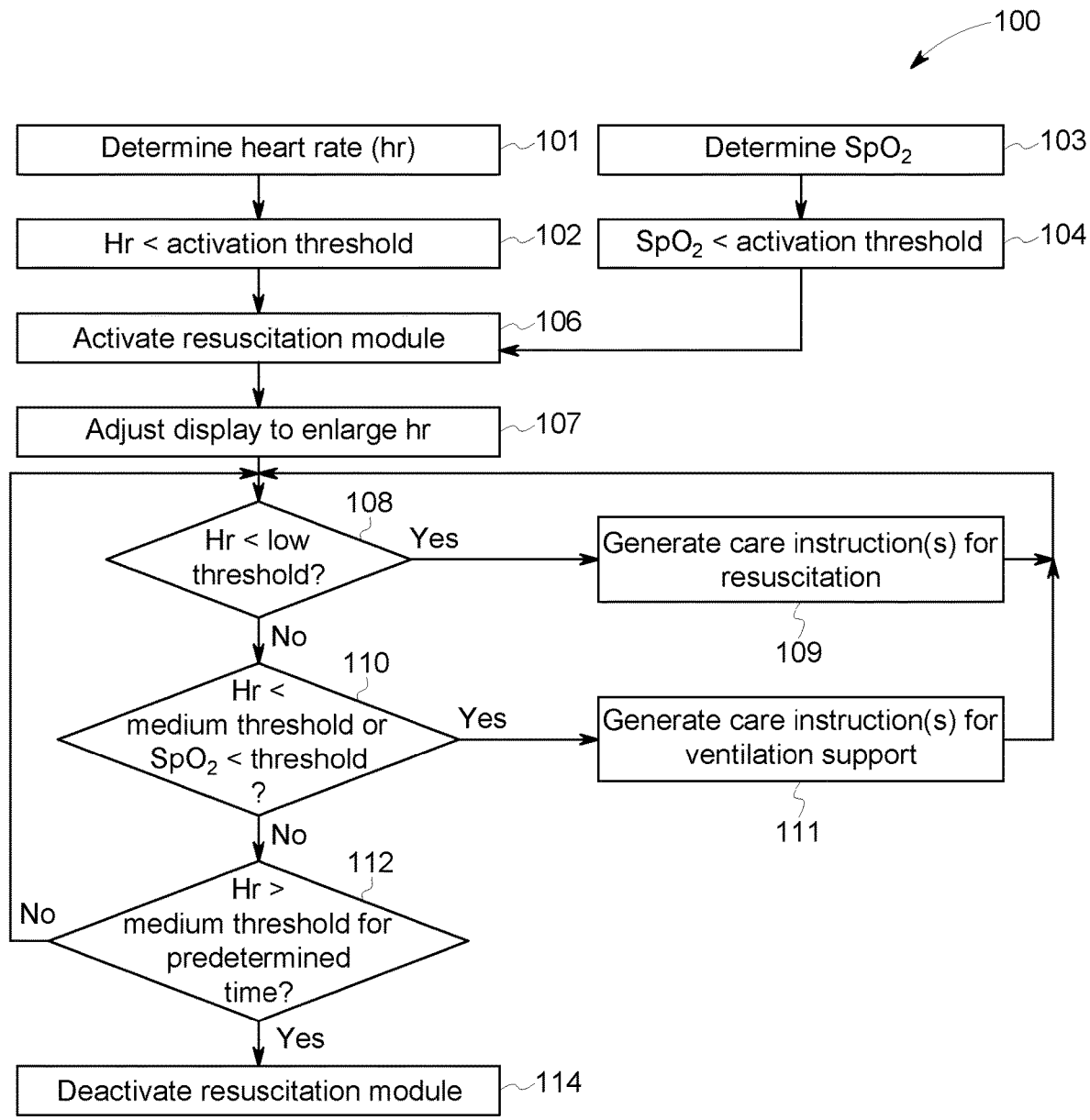
FIGS. 5-9 are flow charts depicting exemplary methods, and portions thereof, of operating an infant warming system according to embodiments of the present disclosure.

FIG. 5 is a flow chart exemplifying one embodiment of method 100 of operating an infant warming system which may be executed within the control system of the infant warming system 10, including by the ECG monitor 25, the pulse oximeter device 22, the computing system 200. Immediately upon delivery, the infant 2 is placed on the platform 18. ECG electrodes 28 may be then promptly attached to the infant's torso as the infant is being dried and the airway being cleared, particularly if there is any reason for concern regarding the infant's health status or a need for respiratory or resuscitative care. The $SpO_2$ sensor 23 may also be attached to the infant 2, such as on the infant's foot. A heart rate 80 is determined for the infant, such as by heart rate module 30, at step 101. The heart rate 80 is compared to an activation threshold for the heart rate at step 102. A $SpO_2$ is determined at step 103 and compared to an activation threshold at step 104. If either the heart rate or the $SpO_2$ are below the respective activation threshold, then the resuscitation module 32 is activated at step 106. The activation thresholds are set for the heart rate and $SpO_2$ to provide a value below which the infant is at risk for needing resuscitation and/or respiratory assistance. The activation thresholds may be preset values set within the software executed by the control system, or may be clinician-set values or values established upon configuration of the software within the warming system 10. To provide just one example, the activation threshold for the heart rate may be 100 beats per second; and the activation threshold for the $SpO_2$ will be based on targeted saturations between 60-95% during the first ten minutes of life. In certain embodiments, the resuscitation module 32 may be activated based only on the heart rate value, or based on the heart rate in combination with any other physiological value measured from the infant 2.

Figure 4A:
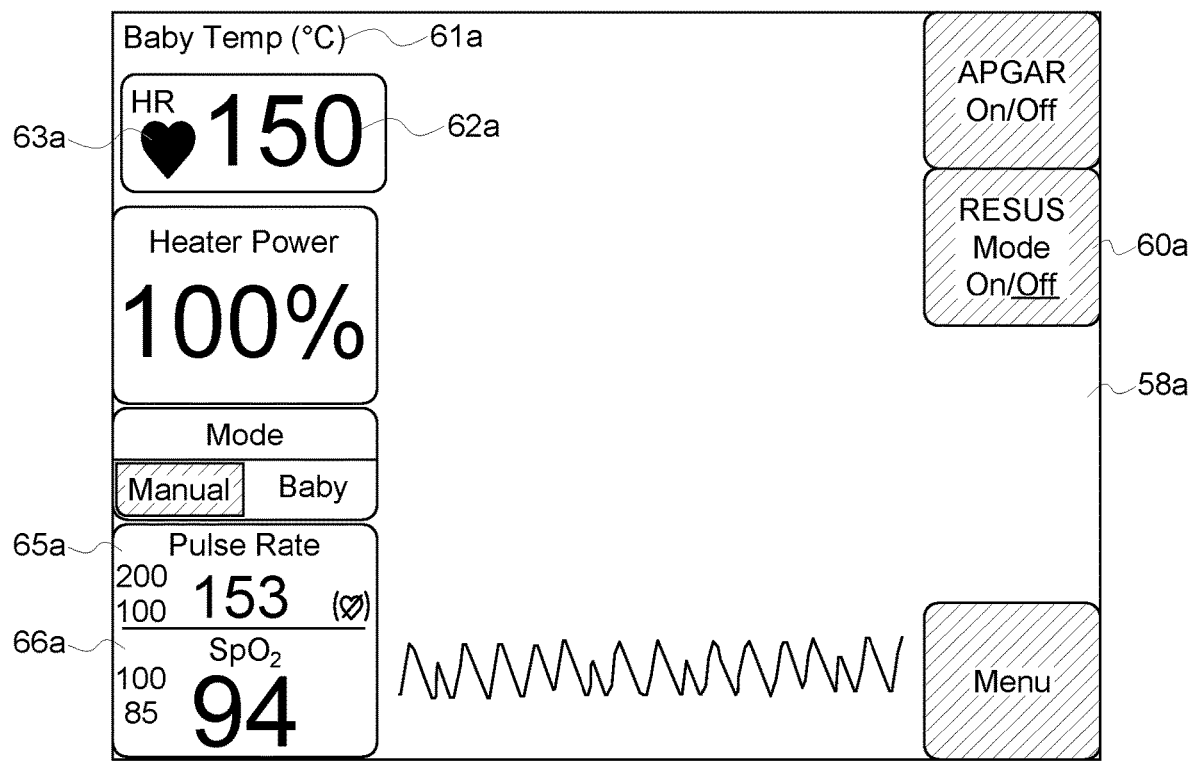
FIGS. 4A through 4C depict exemplary user interfaces on display devices of infant warming systems according to the present disclosure.
Figure 4B:
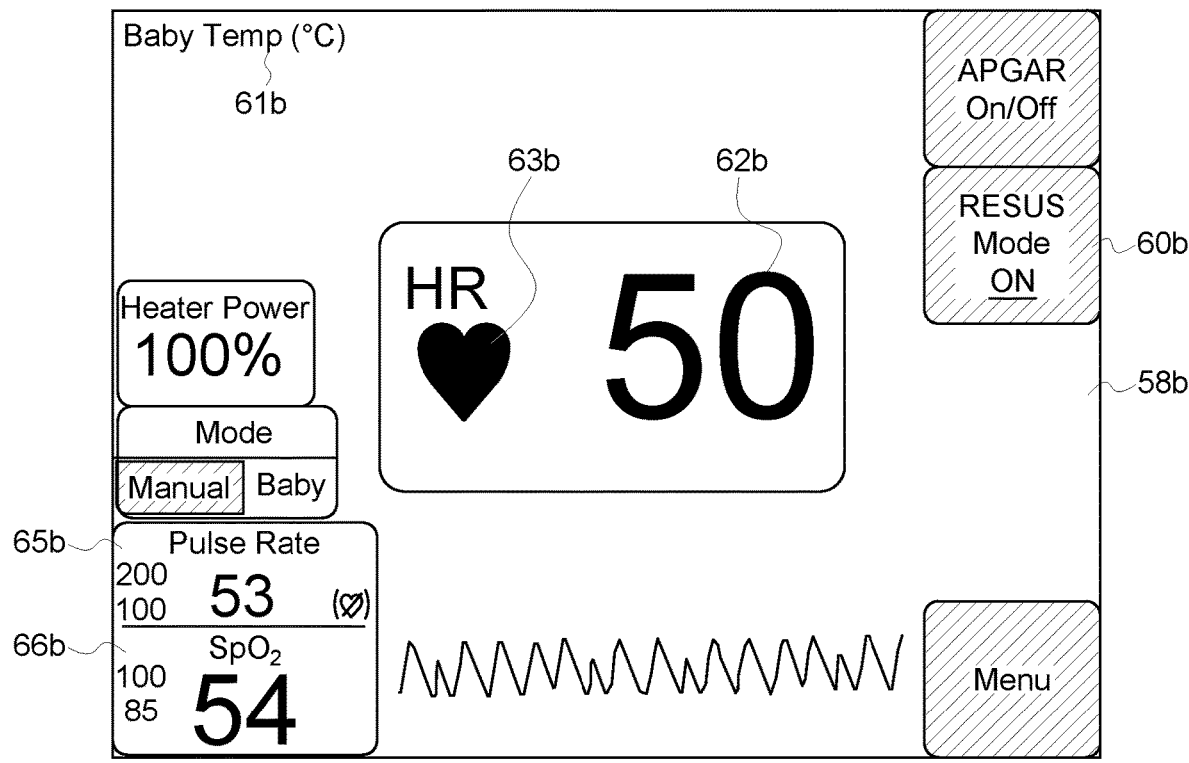
Figure 4C:
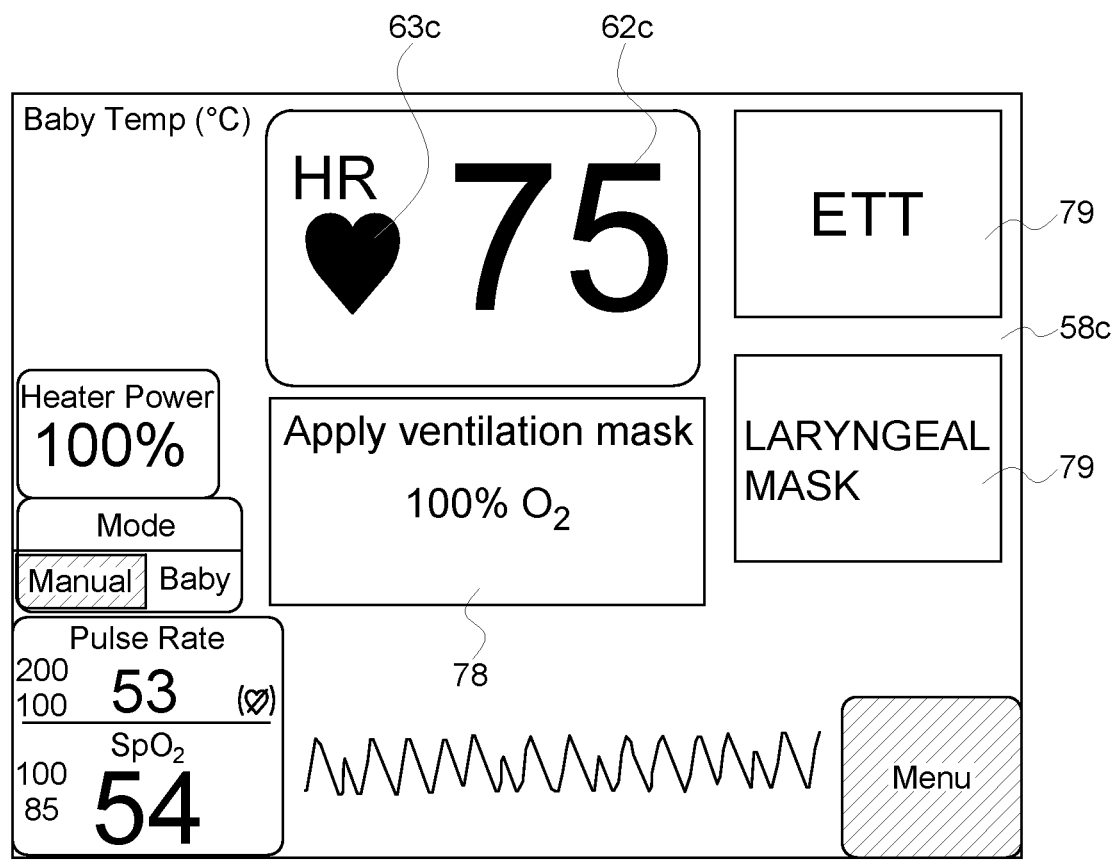

Once the resuscitative module 32 is activated, instructions are executed at step 107 to adjust the display to enlarge the heart rate value depiction thereon. FIGS. 4A-4C provide exemplary embodiments of displays which may be provided on the display device 46 of the warming system 10, with FIGS. 4B and 4C representing exemplary displays where the heart rate value is enlarged compared to its presentation when the control system is not operating in resuscitation mode. FIG. 4A depicts an exemplary display screen 58a which may be shown on the display device 46 during normal operation of the infant warming system 10, or operation of the infant warming system 10 in a mode other than resuscitation mode. The display screen 58a provides various physiological measurement value indicators on the left hand side, including the infant's temperature value display 61a, the heart rate value display 62a, the heart rate icon 63a, the pulse rate value display 65a, and the $SpO_2$ value display 66a. The various physiological values are provided so that they are all visible on the left hand side of the screen without any one value being significantly larger than the others. On the right hand side of the display screen 58a, various mode indicators and/or mode selection control buttons (if the display screen 58a is on a touch screen). A resuscitation mode display 60a and/or selection button is provided indicating that the system is not operating in resuscitation mode and that the resuscitation module 32 is off and is not active. In an embodiment where the display device 46 is a touch screen, the area of the resuscitation mode display 60a may also be a selection button wherein the clinician can touch to provide a resuscitation mode selection 72 input in order to active the resuscitation module 32. Whereas other mode indicators, including an APGAR mode indicator and a menu button are also shown on the exemplary display screen 58a.

FIG. 4B depicts a second display screen 58b embodiment which may be shown on the display device 46 when the infant warming system 10 is operating in resuscitation mode, and thus when the resuscitation module 32 is active. Most notably, the heart rate value display 62b and heart rate icon 63b are enlarged and moved to the center of the display screen 58b to become the focal point so that the clinician can easily identify and focus on the heart rate value. In certain embodiments, other values may be removed or made smaller on the display screen 58b so that the heart rate value is the focal point and visual distractions can be reduced or eliminated so that the clinician can immediately recognized and focus on the heart rate value. In certain embodiments, the pulse rate value display 65b and the $SpO_2$ value display 66b may remain reasonably visible as the clinician may want a visual indicator of those values as well, however such values are not provided in a way to distract from or be visually confusing with the heart rate value display 62b. The resuscitation mode selection button 60b indicates that the resuscitation mode is on. Certain elements or aspects of the display may be made smaller in order to avoid crowding the heart rate value display 62b and to make the heart rate value display 62b more prominent, such as the manual/baby mode indicator and the heater power indicator in the example of FIGS. 4A and 4B. Moreover, the movement and enlargement of the heart rate value display into the prominent position at the center of the display screen 58b provides the primary visual indicator to the clinician that the resuscitation module 32 is active and the control system is operating in the resuscitation mode. In certain embodiments, the heart rate icon 63 may be a blinking icon that blinks, enlarges, or otherwise changes corresponding to each detected heart beat. Thus, the resuscitation mode display screen 58b may provide a visual indicator of each detected heart beat to provide an additional input to the clinician regarding heart rate 80. Alternatively or additionally, the resuscitation module 32 may be configured or configurable to generate an audible tone for each detected heart beat, such as a heart beat sound, and/or to generate an audible enunciation of the heart rate for the clinician. Therefore, the clinician can focus on caring for the infant 2 and can be provided the heart rate information without having to look at the display screen 58b.

FIG. 4C provides another embodiment of a display screen 58c for operation in the resuscitation mode. In that embodiment, the display screen 58c includes a care instruction display 78 displaying one or more care instructions 84 generated by the resuscitation module 32, such as the most recent care instruction or the care instructions provided at the current care stage 82. In embodiments where the display device 46 is a touch screen, the care instruction display 78 may also provide a selection button that the clinician can touch in order to provide acknowledgement of executions 74 of the care instruction 84 indicated by the care instruction display 78. One or more care option displays 79 may also be provided to display the current care options 86 generated by the resuscitation module 32 based on the heart rate 80 and/or the care stage 82. In the depicted embodiment, the care option displays 79 suggest two possible care options 86, or care routes, including administration of an endotracheal tube or administration of a laryngeal mask. Should the clinician determine that either of those care options 86 indicated by the care option displays 79 should be executed, the clinician may provide a care option selection 76 input to inform the system that the clinician is going to perform said care option 86. In certain embodiments where the display screen 58c is shown on a touch screen, as described above, the care option displays 79 may also provide selection buttons wherein the clinician can provide a care option selection input 76 by touching the respective care option display area 79 in accordance with the care option 86 being selected. In certain embodiments, the system 10 may alternatively or additionally be configured to receive a care option selection 76 via an audible enunciation or instruction received via the microphone 14.

Returning to FIG. 5, upon activation of the resuscitation module 32 instructions are executed to compare the heart rate and/or SpO$_2$ to various thresholds in order to determine and generate care instruction to provide guidance in caring for the infant 2. In the example, instructions are executed at step 108 to compare a heart rate value such as a current heart rate measurement to a low heart rate threshold indicating that the infant is in need of resuscitative care. To provide just one example, the low heart rate threshold may be 60 beats per minute. If the infant's heart rate is below the low heart rate threshold, then care instructions for resuscitation are generated at step 109. For example, visual instructions may be provided on the visual display device 46 and/or audible instructions may be generated via the speaker 16 providing guidance to the clinician for administering respiratory support, such as by incubating the infant, and/or instructing the clinician to perform chest compressions on the infant. If the heart rate is not below the low threshold, then the instructions are executed at step 110 to determine whether the heart rate is below a medium threshold. Instructions may also be executed to determine whether the SpO$_2$ is below a threshold SpO$_2$ level which may be the same or different value than the activation threshold. If one or both of the heart rate or SpO$_2$ values are below their respective thresholds, then instructions are executed at step 111 to generate care instructions for ventilation support. For example, instructions may be generated on the display device 46 or via the speaker 16 regarding application of a ventilation mask to the infant 2 and/or supplying a particular oxygen level (e.g., O$_2$%). In other embodiments, the ventilation support instructions may be based on heart rate alone, without examination of SpO$_2$, or based on heart rate in combination with other parameter measurements. The heart rate is continually monitored and, if the heart rate changes, instructions are provided accordingly. If the heart rate remains above the medium threshold for at least a predetermined time, which is represented at step 112, then the infant is deemed to no longer need, or potentially need, resuscitation support and the resuscitation module 32 is deactivated at step 114.

Figure 6:
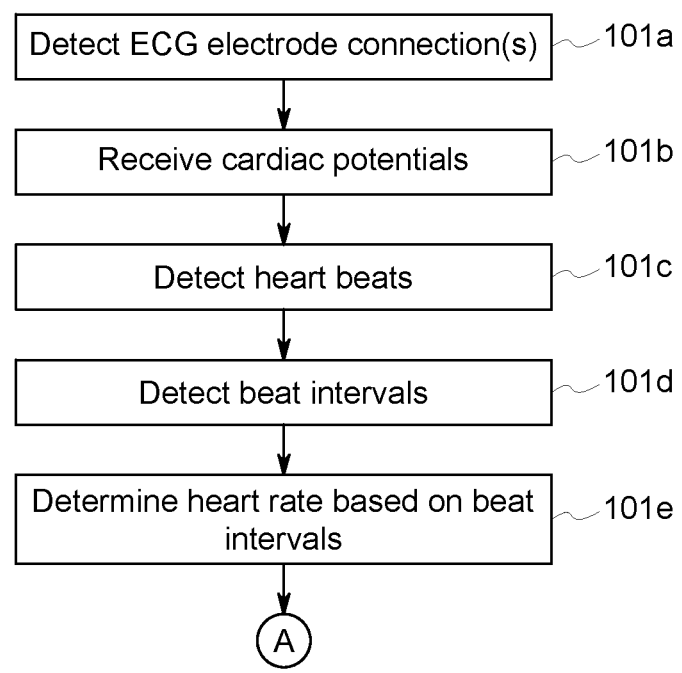

FIG. 6 is a flow chart depicting one embodiment of method steps determining heart rate 80, represented in FIG. 5 as step 101. One or more ECG connections are detected at step 101A such as by impedance measurement to verify that the two or more ECG electrodes 28 are sufficiently attached to the infant 2 to receive reliable cardiac potentials. In certain embodiments, lead off alerts may be provided where the impendence is especially high, such as above an impedance threshold, indicating that the ECG electrodes 28 are disconnected or not sufficiently connected to the infant 2. Cardiac potentials are received at step 101b from the measurements by the ECG electrodes 28. The cardiac potentials in each of one or more leads are then analyzed at step 101c to detect heart beats within the data. For example, heart beats may be identified based on identification of some or all of the QRS wave forms, such as detection of at least the R wave. Beat intervals are then determined at step 101d, such as by determining the R-R interval between each identifiable QRS wave form. The heart rate is then determined at step 101e based on the beat intervals. For example, the heart rate may be an average of the beat intervals in the various leads and/or a filtered or averaged value calculated based on a predetermined number of recent beat interval values.

The heart rate determination may be performed, for example, by a heart rate module 30, such as computer executable instructions to carry out the steps depicted in FIG. 6. Some or all of the instructions encompassed in the heart rate module 30 may be incorporated and executed on a separate ECG monitor 25, or some or all of the foregoing instructions may be stored on and/or executed within the computing system 200 of the infant warming system 10.

Figure 7:
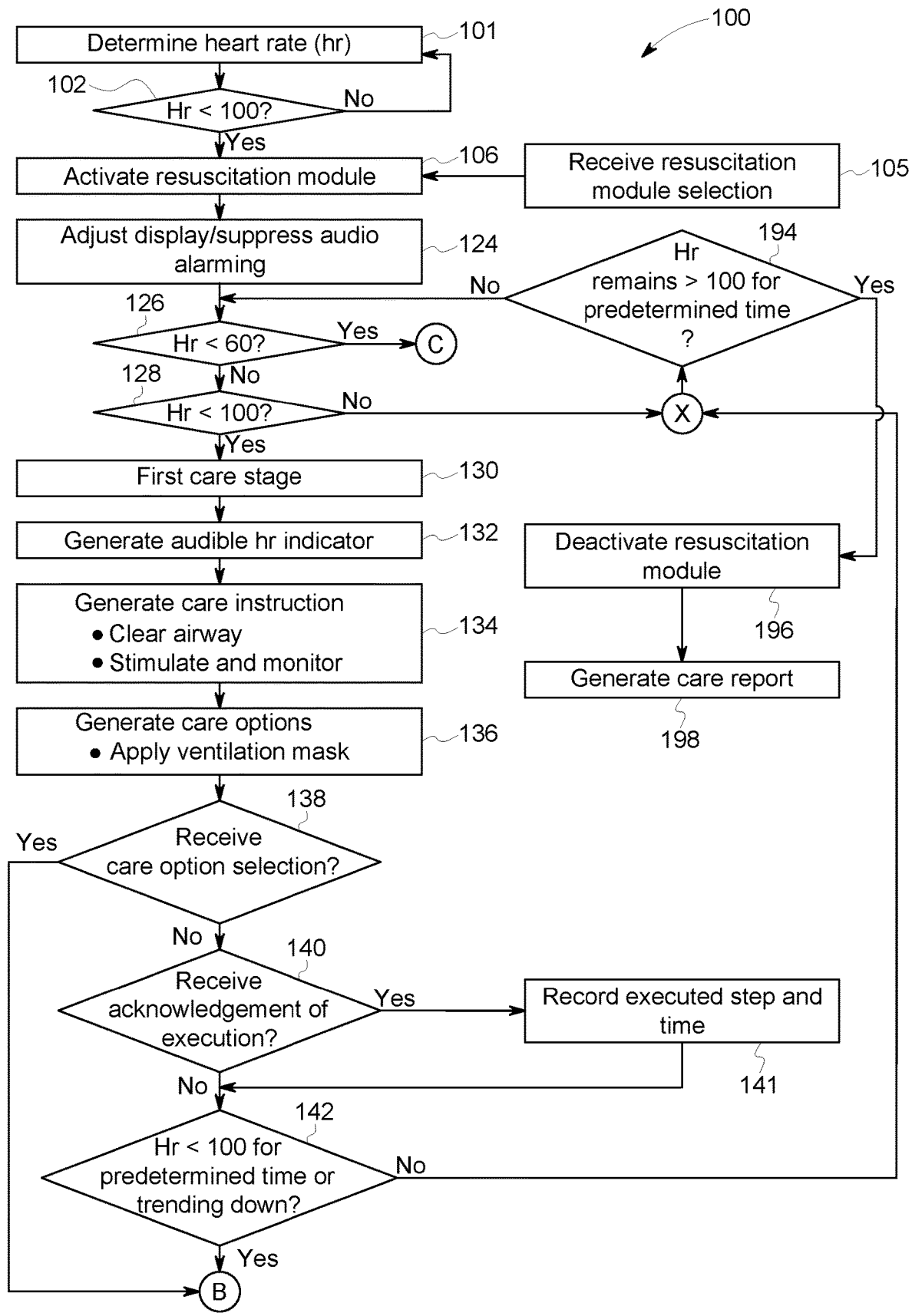
Figure 8:
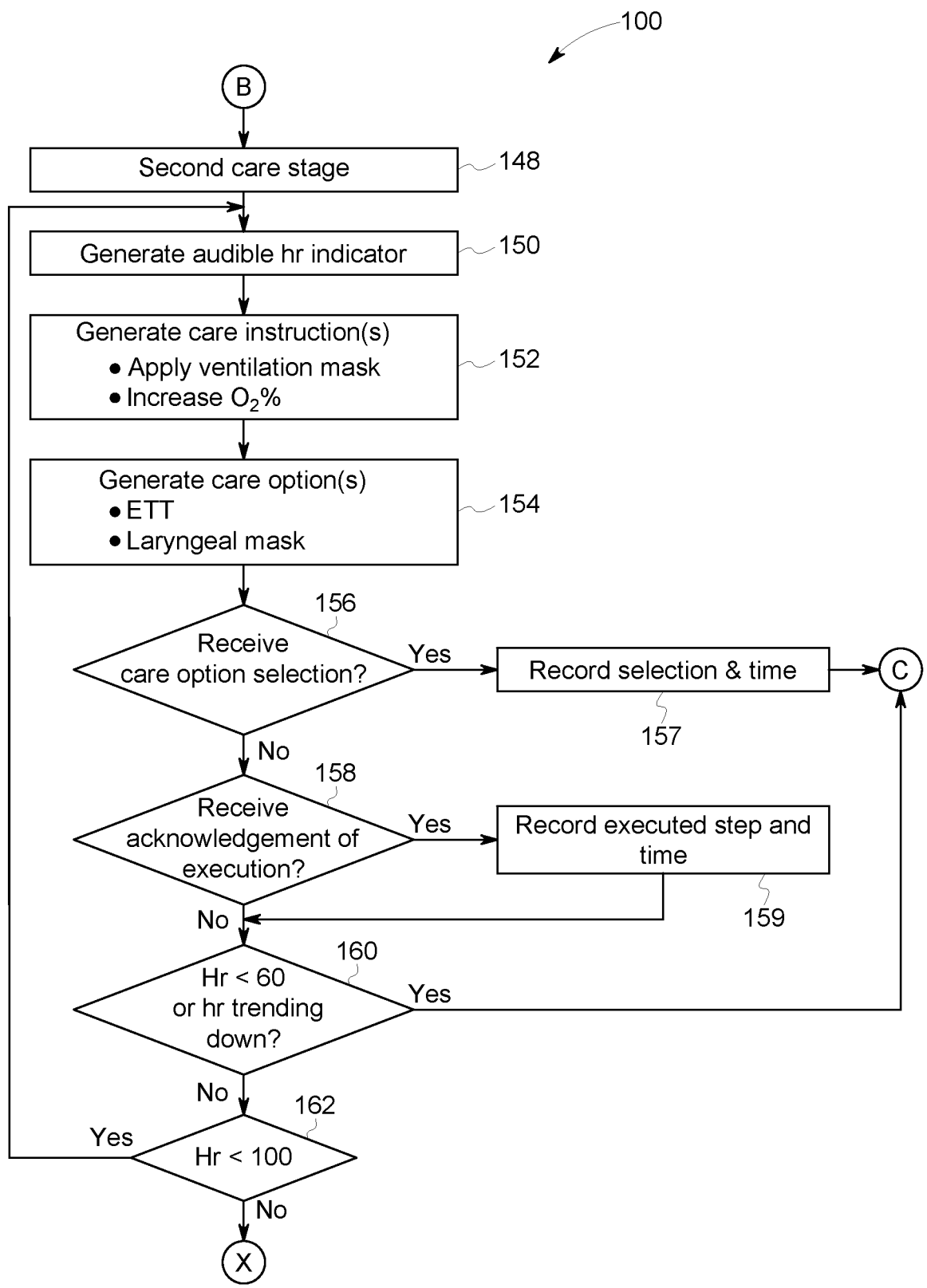
Figure 9:
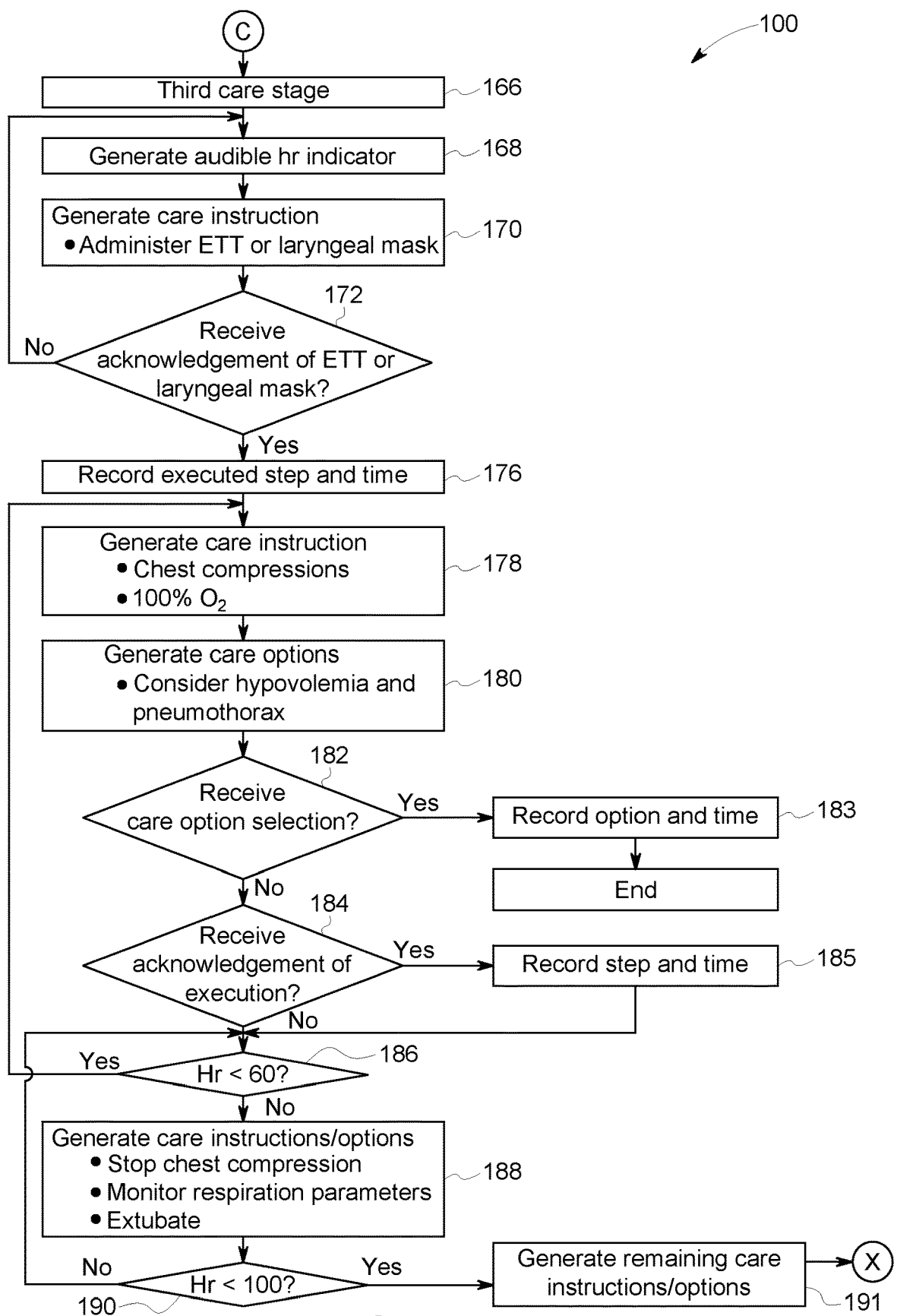

FIGS. 7 through 9 depict additional embodiments of methods 100, or portions thereof, of operating an infant warming system 10 to provide resuscitation assistance to a clinician caring for an infant immediately upon birth, such as care provided in the first twenty minutes of the infant's life. For example, the flow charts at FIGS. 7 through 9 provide exemplary method steps effectuated by executing instructions of the resuscitation module 32 within the computing system 200. The heart rate is determined at step 101, such as by the heart rate module as described above. The determined heart rate is then compared to a threshold, such as an activation threshold of 100 beats per minute, at step 102. For example, the comparison step 102 may be performed by executing instructions incorporated as part of the heart rate module 30.

If the heart rate is below 100 beats per minute, or if a resuscitation module selection 72 is received, represented at step 105, then the resuscitation module 32 is activated at step 106. Steps are then executed to adjust the display, such as to enlarge and modify the heart rate value display 62, which is represented at step 124. Instructions may also be executed at step 124 to suppress alarm annunciation, or audio alarms, such as to eliminate some or all audio alarms and alerts normally generated by the system. This allows the clinician can focus on resuscitation and the care instructions provided by the resuscitation module 32 without distraction and without having to deal with silencing other alarms that may be redundant or superfluous to instructions and alerts provided by the resuscitation module 32. In certain embodiments, the resuscitation module 32 may be configured such that all auditory alerts and alarming is eliminated other than that provided by the resuscitation module 32 during its operation. In other embodiments, the alarm suppression may be configurable by a clinician, such as upon set up of the infant warming system 10 and/or by a clinician prior to operating the infant warming system 10 (such as through a system set up screen). Accordingly, the system may be configurable to suppress some alarms, such as low level alarms or technical alarms, while allowing others, such as allowing certain critical alarms. To provide just one example, the system may be configured to allow an auditory alert regarding an electrode disconnection, or "lead off" alert regarding the ECG electrodes 28 so that a clinician can be made aware if one of the ECG electrodes 28 is no longer sufficiently connected to receive reliable cardiac potentials 70, and thus a reliable heart rate cannot be determined and the resuscitation module 32 is unable to provide proper guidance.

Step 126 is then executed to determine whether the heart rate is below 60 beats per minute. If so, then the system proceeds immediately to the third care stage and associated steps depicted at FIG. 9. If the heart rate is greater than 60 beats per minute, then steps are executed at step 128 to determine whether the heart rate is less than 100 beats per minute. If not, then instructions are executed, represented at step 194, to make sure that the heart rate remains above 100 beats per minute for at least a predetermined time to determine that the infant is not in need of resuscitative or ventilation support before deactivating the resuscitation module at step 196. If the heart rate is between 60 beats per minute and 100 beats per minute, then the resuscitation module enters a first care stage at step 130. An audible heart rate indicator is generated at step 132, such as an audible tone corresponding to the time of each detected heart beat and/or an audible enunciation of the heart rate. A care instruction is generated at step 134 providing guidance regarding initial care and monitoring of the infant in the first seconds and minutes after birth. For example, a care instruction 84 may be provided on the display device 46 and/or enunciated by the speaker 16 instructing a clinician to clear the infant's airway and/or to stimulate and monitor the infant to determine whether the infant's breathing and heart rate is increasing.

The resuscitation module 32 may further generate care options 86 at step 136 providing guidance on possible alternative or next steps. For example, care options may be provided on the display device 46, such as that exemplified by the display screen 58C of FIG. 4C, providing cues indicating care options 86 to the clinician. Alternatively or additionally, care options may be enunciated via the speaker 16. A care option selection 76 may be received at step 138, such as via selection of a care option selection button 79 on the display device 46 by a clinician who has determined that additional care is needed for the infant. Depending on the care option selection 76 received at step 138, the resuscitation module may proceed to the second care stage represented at FIG. 8. In certain embodiments, this resuscitation module 32 may further execute steps to record the care option selected and the time of selection in order to record the selection, including the time of selection, in the care record.

Alternatively or additionally, the system may receive an acknowledgment of execution 74 of a care instruction at step 140, such as via the touch screen display device 46 and/or via the microphone 14 as is described above. If an acknowledgement of execution 74 is received, then step 141 is executed to record the executed step and the time of execution in a care record. Step 142 is then executed to access whether the heart rate has remained below 100 for a predetermined time indicating that the condition of the infant 2 is not improving and that the infant may require further support, or that the heart rate is trending downward at least a predetermined rate which also indicates that the infant 2 may be in need of further support. If either condition is satisfied, then the resuscitation module 32 progress to the second care stage exemplified at FIG. 8. If that is not the case and the heart rate is improving and/or has exceeded 100 beats per minute, then the resuscitation module 32 moves to step 194 to determine whether deactivation of the resuscitation module 32 is appropriate.

While the resuscitation module 32 remains in the first care stage, multiple audible heart rate indicators may be generated at step 132, such as periodically, and step 134 may be re-executed to provide additional or subsequent care instructions. For example, the care instructions may increase the intervention level over time or as the system receives acknowledgements of execution 74 of certain care instructions. The resuscitation module 32 remains in the first care stage, either for a predetermined time while the heart rate remains below 100 or based on the heart rate trending downwards at a predetermined rate or falling below 60 beats per minute.

FIG. 8 depicts an exemplary set of steps that may be executed by the resuscitation module 32 during a second care stage. The second care stage is received and acknowledged at step 148. For example, the resuscitation module 32 may record the time that the second care stage was imitated in the care record. Additionally, notification of the second care stage may also be provided on the display device 46 or enunciated via the speaker 16. An audible heart rate indicator is generated at step 150, such as an audible enunciation of the heart rate and/or a tone, such as a pulse tone, corresponding to the timing of each detected heart beat, so that the clinician can be advised of the heart beat without having to look at the display device 46. Care instructions are generated at step 152 that are appropriate for the care stage and/or the infant's heart rate. For example, care instructions may be visually and/or audibly presented to instruct the clinician to apply a ventilation mask to the infant in order to supply ventilation support.

Alternatively or additionally, care instructions may be generated to increase the oxygen percentage, if appropriate. For example, care instructions may be first provided to apply a ventilation mask and, upon receipt of an acknowledgement of execution 74 of that step or after a predetermined period of time, a second care instruction may be provided to instruct the clinician on increasing the oxygen and/or an appropriate $O_2$ percent based on the heart rate and/or the period of time for which the heart rate has been low.

Care options may also be presented at step 154 representing additional and/or increased care steps. For example, care options may be presented in the second care stage advising the clinician of next steps if the infant's condition is deteriorating. Based on their judgement, the clinician may advance to the third care stage by providing a care option selection 76, examples of which are described above. If a care option selection is received at step 156, then a record is made in the electronical care record at step 157 of the selected care option and time of selection. The resuscitation module 32 then begins execution of the steps associated with the third care stage, which are exemplified at FIG. 9. If an acknowledgement of execution is received, represented as step 158, then instructions are executed at step 159 in order to record the executed step and the time of execution. Instructions are executed at step 160 to determine whether the heart rate has fallen below 60 beats per minute or is trending downward at least a predetermined rate. If so, then the resuscitation module 32 progresses to the third care stage. If not, then assessment is made at step 162 on whether the heart rate remains 100 beats per minute. As long as the heart rate remains above 60 and is not trending downward at greater than the threshold rate, then the resuscitation module 32 remains at the second care stage and provides care instructions and care options accordingly. Once the heart rate increases to at least 100 beats per minute, then the resuscitation module 32 progresses to step 194 to assess whether deactivation is appropriate.

FIG. 9 depicts exemplary steps that may be executed by the resuscitation module 32 operating in an exemplary third care stage. The resuscitation module enters the third care stage at step 166. As explained above, the time of beginning the third care stage may be automatically recorded in the care record by the resuscitation module. An audible heart rate indicator may be provided at step 168 and one or more care instructions 84 may be generated at step 170, such as via the display device 46 and/or via the speaker 16. For example, an initial care instruction may be generated instructing a clinician to support respirations by placing an endotracheal tube or laryngeal airway mask. The resuscitation module 32 may then wait for acknowledgment of placement of the endotracheal tube or laryngeal airway mask at step 172, and may repeat the audible heart rate indicator and/or the care instruction periodically until such acknowledgment is received.

Once an acknowledgment of execution of placement of the endotracheal tube or the laryngeal airway mask is received at step 172, then the executed step and time are recorded at step 176 and further care instructions are provided at step 178, such as to start chest compressions and/or provide oxygen. Care options are generated at step 180. For example, at the third care stage the care options 86 may include consideration of underlying conditions which may require surgical or other interventions, such as considering hypovolemia or pneumothorax, for example. If a care option selection is received at step 182, a record is made of the selection and the time of selection at step 183 in the care record and the resuscitation module 32 may be promptly ended to make way for further emergency intervention and/or care as directed by the clinician.

If an acknowledgment of execution is received at step 184, record is automatically made in the care record at step 185. For example, the speech detection module 34 may detect a statement made by the clinician acknowledging performance of the care instructions, such as chest compressions. For instance, the speech detection module 34 may be configured to look for speech related to performance of chest compressions, such as by identifying any of a set of predefined words or phrases. In certain embodiments, the words or phrases identified by the speech detection module 34 may vary based on the care stage—i.e., based on the expected inputs from the clinician. Similarly, the resuscitation module 32 may be configured to interpret the output of the speech detection module 34 differently based on the care stage and the expected inputs from the clinicians based on the current state of the infant and the care being performed. If such keywords or phrases are detected in the recording by the microphone 14 by the speech detection module 34, then the resuscitation module 32 may detect an acknowledgment of execution 74. For example, the speech detection module 34 may detect the clinician's statement of "performing chest compressions" and pass that to the resuscitation module 32, which interprets that as an acknowledgment of execution 74 of the respective care instruction.

The care instructions and options continue so long as the heart rate remains below 60 beats per minute and no additional care option is selected at step 182. If the heart rate increases to 60 beats per minute or above, then care instructions and options are generated accordingly, represented at step 188. In certain embodiments, the resuscitation module 32 may enter a fourth care stage at this juncture, as the resuscitation module 32 may be configured to pass through any number and arrangement of care stages.

In either embodiment, care instructions and options are generated to guide the clinician on performing care steps as the heart rate increases. Once the heart rate exceeds 100 beats per minute at step 190, remaining care instructions and options are presented, represented at step 191, such as extubation and/or other care steps which may be necessary following the extubation. The resuscitation module 32 then proceeds to step 94 to determine whether deactivation of the resuscitation module 32 is appropriate.

Once the resuscitation module is deactivated, the care report is generated at step 198 based on or including the care record—the record over time of certain inputs and outputs of the resuscitation module 32. For example, the heart rate values may be recorded at predetermined intervals or at certain stages, such as each time a threshold value is crossed and/or each time an audible heart rate indicator is provided. In certain embodiments, the care record may be accessible and/or displayed to a clinician for editing, such as during the post care analysis and debriefing phase when reports are being reviewed and generated.

Referring again to FIG. 3, a system diagram of an exemplary computing system 200 on an infant warming system 10 is shown. The computing system 200 that includes a processing system 206, storage system 204, software 202, and communication interface 208. The system diagram shows the computing system 200 has having software 202 encompassing the heart rate module 30, the resuscitation module 32, and the speech detection module 34. The processing system 206 loads and executes software 202 from the storage system 204, including modules 30, 32, 34 which are applications within the software 202. Each of the modules 30, 32, 34 include computer-readable instructions that, when executed by the computing system 200 (including the processing system 206), direct the processing system 206 to operate as described herein in further detail.

Although the computing system 200 as depicted in FIG. 3 includes one software 202 encapsulating heart rate module 30, one resuscitation module 32, and one speech detection module 34, it should be understood that one or more software elements having one or more modules executed by one or more processing systems may provide the same operation. For example, in certain embodiments the heart rate module 30 (or a portion thereof) may be stored on and executed by a separate computing system comprising an ECG monitor 25 that is separate from the computing system 200. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes a processor, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204 can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as with the ECG monitor 25 (i.e., to receive the cardiac potentials 70 and/or the heart rate 80, if the ECG monitor 25 is configured to provide such calculation), the pulse oximeter device 22 (i.e., to receive the $SpO_2$ value), and with various user interface controllers for the display device 46, speaker 16, and/or microphone 14 (i.e., to receive the various selection or acknowledgement inputs from the clinician and generate the various instructions and options described herein).

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. An infant warming system comprising:
   a platform for supporting an infant;
   at least two chest electrodes configured to connect to and detect cardiac potentials from a chest of the infant;
   an ECG monitor configured to receive the cardiac potentials from the at least two chest electrodes and determine a heart rate based on the cardiac potentials;
   a pulse oximeter device configured to determine an $SpO_2$ for the infant;
   a processor configured to:
   compare the heart rate for the infant to a first heart rate threshold and compare the $SpO_2$ for the infant to a first $SpO_2$ threshold;
   adjust a display of the heart rate and the $SpO_2$ on a display device based on the comparisons;
   generate a first care instruction for a first care stage via a user interface based on the heart rate of the infant, the $SpO_2$ of the infant, or a combination thereof;
   determine a second care stage following execution of the first care instruction, wherein the heart rate or the SpO2 remains below a predetermined threshold; and
   generate a second care instruction based on the second care stage.

2. The infant warming system of claim 1, wherein the processor is to receive acknowledgment of execution of the first care instruction.

3. The infant warming system of claim 1, wherein the processor is to:
   determine one or more activation thresholds based on the $SpO_2$ for the infant, wherein the one or more activation thresholds comprise at least the first $SpO_2$ threshold;
   generate a third care instruction via the user interface based on the $SpO_2$ for the infant and the one or more activation thresholds.

4. The infant warming system of claim 3, wherein the one or more activation thresholds are preset values set within software executed by the processor or values established upon configuration of the software within the infant warming system.

5. The infant warming system of claim 3, wherein the processor is to calculate the one or more activation thresholds based at least in part on a time of life of the infant.

6. The infant warming system of claim 3, wherein the one or more activation thresholds represent one or more target saturation levels for the infant.

7. The system of claim 3, wherein the user interface includes a speaker and the first and/or the second care instruction comprises an audible instruction of the SpO2 of the infant.

8. The system of claim 7, wherein the processor is further configured to automatically suppress audio annunciation of one or more threshold alarms.

9. The system of claim 7, wherein the first care instruction, the second care instruction, or a combination thereof includes a visual instruction.

10. The system of claim 1, wherein the processor is further configured to:
    determine one or more care options based on the SpO2 of the infant; and
    display the determined one or more care options on the display device.

11. The system of claim 10, wherein the infant care station further comprises a microphone to record audible inputs from a user; and
    wherein the processor is further configured to:
        detect an acknowledgment of execution of the one or more care options, wherein the detecting comprises detecting an audible care option selection recorded by the microphone.

12. A method of operating an infant warming system, comprising:
    detecting a connection of at least two ECG chest electrodes, wherein the at least two ECG chest electrodes detect cardiac potentials from a chest of an infant;
    determining, using an ECG monitor, a heart rate for the infant based on the cardiac potentials sensed via the ECG chest electrodes;
    comparing the heart rate for the infant to a first heart rate threshold and comparing an $SpO_2$ for the infant to a first $SpO_2$ threshold;
    adjusting a display of the heart rate and the $SpO_2$ on a display device based on the comparisons;
    generating a first care instruction for a first care stage via a user interface based on the heart rate for the infant, the $SpO_2$ for the infant, or a combination thereof;
    determining a second care stage following execution of the first care instruction, wherein the heart rate or the SpO2 remains below a predetermined threshold; and
    generating a second care instruction based on the second care stage.

13. The method of claim 12, further comprising:
    receiving acknowledgment of execution of the first care instruction.

14. The method of claim 12, further comprising:
    determining one or more activation thresholds based on the $SpO_2$ for the infant;
    generating a third care instruction via the user interface based on the $SpO_2$ for the infant and the one or more activation thresholds.

15. The method of claim 14, wherein the one or more activation thresholds are preset values set within software executed by a processor or values established upon configuration of the software within an infant warming system.

16. The method of claim 14, further comprising calculating the one or more activation thresholds based at least in part on a time of life of the infant.

17. The method of claim 14, wherein the one or more activation thresholds represent one or more target saturation levels for the infant.

18. The method of claim 14, wherein providing the first care instruction, the second care instruction, or a combination thereof comprises providing an audible instruction based on the SpO2 of the infant patient.

* * * * *